(12) United States Patent
Paoletti et al.

(10) Patent No.: US 8,951,991 B2
(45) Date of Patent: *Feb. 10, 2015

(54) POLYMER MIXTURES OF ANIONIC AND CATIONIC POLYSACCHARIDES AND USE THEREOF

(75) Inventors: Sergio Paoletti, Trieste (IT); Ivan Donati, Sedegliano (IT); Eleonora Marsich, Trieste (IT)

(73) Assignee: Universita Degli Studi di Trieste, Trieste (IT)

( * ) Notice: Subject to any disclaimer, the term of this patent is extended or adjusted under 35 U.S.C. 154(b) by 1036 days.

This patent is subject to a terminal disclaimer.

(21) Appl. No.: 12/301,552

(22) PCT Filed: May 21, 2007

(86) PCT No.: PCT/EP2007/054860
§ 371 (c)(1),
(2), (4) Date: Nov. 19, 2008

(87) PCT Pub. No.: WO2007/135116
PCT Pub. Date: Nov. 29, 2007

(65) Prior Publication Data
US 2009/0197832 A1 Aug. 6, 2009

(30) Foreign Application Priority Data

May 22, 2006 (IT) .............................. PD2006A0202

(51) Int. Cl.
| | | |
|---|---|---|
| *A61K 31/722* | (2006.01) | |
| *A61P 29/00* | (2006.01) | |
| *A61L 27/20* | (2006.01) | |
| *A61L 27/52* | (2006.01) | |
| *C08L 1/28* | (2006.01) | |
| *C08L 5/00* | (2006.01) | |
| *C08L 5/04* | (2006.01) | |
| *C08L 5/06* | (2006.01) | |
| *C08L 5/08* | (2006.01) | |
| *C08L 5/10* | (2006.01) | |
| *C08L 5/12* | (2006.01) | |

(52) U.S. Cl.
CPC ................ *A61L 27/20* (2013.01); *A61L 27/52* (2013.01); *C08L 1/286* (2013.01); *C08L 5/00* (2013.01); *C08L 5/04* (2013.01); *C08L 5/06* (2013.01); *C08L 5/08* (2013.01); *C08L 5/10* (2013.01); *C08L 5/12* (2013.01)
USPC .......................................................... 514/55

(58) Field of Classification Search
None
See application file for complete search history.

(56) References Cited

U.S. PATENT DOCUMENTS

| | | | | |
|---|---|---|---|---|
| 5,578,578 A | * | 11/1996 | Hecht et al. ..................... 514/23 | |
| 5,747,475 A | | 5/1998 | Nordquist et al. | |
| 5,958,443 A | | 9/1999 | Viegas et al. | |
| 5,972,326 A | * | 10/1999 | Galin et al. ................. 424/78.04 | |
| 6,277,792 B1 | | 8/2001 | House | |
| 6,756,363 B1 | | 6/2004 | Nordquist et al. | |

FOREIGN PATENT DOCUMENTS

WO 02/40055 A 5/2002

OTHER PUBLICATIONS

Marcon, P. et al "The role of galectin-1 in the interaction between chondrocytes . . . " Biomaterials (2005) vol. 26, pp. 4975-4984.*
Berger, J. et al "Structure and interactions in chitosan hydrogels . . . " Eur. J. Pharm. Biopharm. (2004) vol. 57, pp. 35-52.*
Database CA Chemical Abstracts Service, Columbus, Ohio; "Production of film for treating burns using chitosan"; XP002455236 retrieved from STN database accession No. 142:204900 abstract & KR 2002 014 189A (S. Korea) Feb. 25, 2002.
Donati, I et al.; "The aggregation of pic articular chondrocyte and synthesis of extracellular matrix by a lactose-modified chitosan"; Biomaterials, Elsevier Science Publishers BV., Barking, GB, vol. 26, No. 9, Mar. 2005, pp. 987-998.
Feng, Qian, et al.; "Self-assembly and characterization of polyelectrolyte complex films of hyaluronic acid/chitosan"; Colloids and Surfaces A: Physicochem. Eng. Aspects; 257-258; (2005) pp. 85-88.

* cited by examiner

*Primary Examiner* — Leigh Maier
(74) *Attorney, Agent, or Firm* — Gifford, Krass, Sprinkle, Anderson & Citkowski, P.C.

(57) ABSTRACT

Described in the present application are compositions comprising mixtures of polyanionic polysaccharides and polycationic polysaccharides consisting of oligosaccharide derivatives of chitosan. In the compositions of the invention said mixtures have proven to be soluble in aqueous environments, despite ionic complexes forming between the acid polysaccharides and chitosan derivatives. Said compositions have also demonstrated significant rheological behavior with an unexpected increase in viscosity and viscoelasticity, although the polysaccharides used have relatively low average molecular weights. The said solubility and rheological behavior renders the compositions of the invention particularly advantageous from the biomedical application viewpoint, in particular for viscosupplementation and particularly in the field of articular pathologies and of ophthalmic surgery.

29 Claims, 7 Drawing Sheets coacervates soluble

POLYMER MIXTURES OF ANIONIC AND CATIONIC POLYSACCHARIDES AND USE THEREOF

CROSS REFERENCE TO RELATED APPLICATIONS

This application is the U.S. national phase of PCT/EP2007/054860 filed May 21, 2007, which claims priority of Italian patent application No. PD2006A000202 filed May 22, 2006.

FIELD OF THE INVENTION

The present invention relates to compositions comprising mixtures of polysaccharides consisting of anionic and polycationic polysaccharides, having suitable physico-chemical characteristics, in particular high viscosity and viscoelasticity, and to their biomedical use.

STATE OF THE ART

Polysaccharides are known to be biopolymers of considerable applicative interest for their high biocompatibility and their distinctive physico-chemical properties, and in particular for the viscous behaviour of their aqueous solutions, as is also known that said rheological behaviour is primarily linked to their molecular weight. Of these biopolymers, hyaluronic acid is certainly one of the most interesting biocompatible polymers from the applicative viewpoint and therefore among the most widely used in the biomedical field, as its aqueous solutions have a distinctive rheological behaviour presenting interesting viscosity and viscoelastic characteristics. This polysaccharide is known to have repeating disaccharide units composed of glucuronic acid and N-acetylglucosamine. Due to the presence of the uronic unit in the polysaccharide sequence, hyaluronic acid has a net negative charge at physiological pH (i.e. 7.4), and is therefore a polyanion. It has found wide usage due to its cited characteristics (i.e. viscosity and viscoelasticity) in both the cosmetics and pharmaceutical fields either as such or as a drug delivery system. In particular it has found wide application in the field ophthalmic surgery and of osteoarticular pathologies, where hyaluronic acid is extensively utilized for viscosupplementation of the synovial fluid by virtue of its aforementioned physico-chemical properties. Indeed, concentrated solutions (1-2%) of high molecular weight hyaluronic acid (above 2,000 kDa) have excellent viscoelastic properties together with high viscosity. Such properties render this hyaluronic acid particularly suitable for treating articular pathologies whether of inflammatory or traumatic origin, since it is able to provide and/or restore adequate functioning of the joint itself. The preferred formulation for hyaluronic acid application in the osteoarticular field is as injectable hyaluronic acid solutions administered by the intra-articular route; in this manner its distinctive rheological properties (i.e. viscosity and viscoelasticity) can be made full use of for the purposes of restoring "mechanical" functionality to the joint.

However, obtaining and purifying high molecular weight hyaluronic acid chains of at least 2000 kDa, at the same time avoiding their degradation and the formation of polymers of low molecular weight and/or high polydispersity, involves complex and expensive production processes, which weigh heavily on the total cost of the preparations for use in the aforesaid treatment. To overcome this problem, considerable interest has been directed at the feasibility of increasing the viscosity of lower molecular weight, and hence cheaper, hyaluronic acid solutions, enabling production rejects normally used for low value-added applications (such as in the cosmetics field) to be used with considerable economical benefits. This has resulted in extensive research on hyaluronic acid derivatives, and in particular derivatives crosslinked with various crosslinking agents, with the aim of improving/increasing the rheological behaviour of hyaluronic acids of low average molecular weight.

Other polysaccharides also find wide use due to the viscous properties of their solutions/dispersions in water. The most utilized, in both the pharmaceutical and food industries for their abundance and relative low cost, include alginates and chitosan.

Chitosan is a polysaccharide widely available in nature obtained by chemical deacetylation of chitin, the principle constituent of crustacean exoskeletons. It is mainly composed of glucosamine units interspersed with N-acetyl-glucosamine units, residuals from the chitin treatment. This polysaccharide is not soluble in water unless the pH is lowered to 5 or less, by adding organic or inorganic acids. Lowering the pH allows protonation of the amine groups on the glucosamine residues, hence conferring solubility to the system. In relation to its wide ranging usage, chitosan has become one of the most studied polysaccharides, including chemical aspects, with the aim of improving its properties, particularly viscosity and solubility in water, useful for application purposes. In the last few years, various chitosan derivatives have been obtained by chemical modification of the polymer chain. For these modifications, reactions of the amine residues on the glucosamine units are commonly used. In particular the addition of saccharide units (mono- and oligosaccharides) as side chains has enabled water soluble chitosan derivatives to be obtained without the need to lower the pH to acid values with the consequent problems of polymer degradation.

U.S. Pat. No. 4,424,346 (Hall, L. D. and Yalpani, M.) describes for the first time the synthesis of these derivatives, and their solubility in a non-acid aqueous environment is also described.

In U.S. Pat. No. 6,277,792 (House, R. F.) chitosans modified in a similar manner to those discussed in U.S. Pat. No. 4,424,346 are used, though not in combination with other polymer systems, either in solution or as dispersions, in order to increase the viscosity of aqueous solutions.

In U.S. Pat. No. 5,747,475 (Nordquist, R. E. et al.) biomaterials prepared with chitosan modified with mono- or oligosaccharides are used as immunoadjuvants in immunotherapy treatment based on the use of laser systems combined with sensitising substances.

With the aim of improving the physico-chemical properties, and hence the viscosity and/or viscoelasticity of these polysaccharides, in particular hyaluronic acid, compositions obtained by combining hyaluronic acid and chitosan have also been described.

In WO Patent 2004/022603 (Cho, K. et al.), with the aim of obtaining a hyaluronic acid with improved physico-chemical properties, particularly improved viscoelasticity, derivatives of hyaluronic acid are prepared which are crosslinked to a glycol polymer, essentially PEG or Pluronic, by amide bonds obtained by introducing a suitable amine group onto said glycols. Also described, in a specific example, are hyaluronic acid derivatives crosslinked to a second polysaccharide, i.e. low molecular weight (maximum 5 kDa) chitosan. The crosslinking reaction makes use of a condensing agent such as EDC (N-[3-dimethylaminopropyl]-N'-ethylcarbodiimide chloride) in the presence of NHS (N-hydroxysuccinimide). The crosslinked hyaluronic acid derivatives have a high viscoelasticity and are suitable for all the various typical uses of hyaluronic acid having these physico-chemical characteristics, including its use in viscosupplementation for treatment of articular pathologies. The arrangement identified in the aforementioned patent application allows the two polysaccharides to be combined, utilizing their physico-chemical properties while at the same time improving them by means of a covalent bond without there being only ionic-type associative interactions between the two oppositely charged polysaccharides.

It should be noted that the polycationic nature of chitosan makes compatibility difficult with other polysaccharides and in particular with polyanionic polysaccharides such as hyaluronic acid. In this respect, the combination of an aqueous solution of hyaluronic acid (a polyanion) and one of chitosan (a polycation) allows the instantaneous formation of insoluble coacervates. This is due to the fact that in an aqueous environment strong interactions are established between the positive charges of one and the negative charges of the other. Precipitation/coacervation of the two polysaccharides prevents any formulation thereof as an injectable composition. This coacervation process between basic polysaccharides and acidic polysaccharides is well know and widely described in the literature. For example U.S. Pat. No. 5,620,706 (Severian, D. et al.) describes the coacervation of chitosan and xanthan, a polysaccharide with negative charges on its side-chains, and which is utilized for obtaining insoluble hydrogels.

With the aim of making chitosan more water soluble U.S. Pat. No. 6,756,363 (Nordquist, R. E., Carubelli, R.) generally provides glycated mono- and/or oligosaccharide derivatives of chitosan, and of these the galactose derivative is described as being the preferred derivative for the purposes of the invention. However, in this latter type of reaction the galactose is irreversibly modified to give galactitol. Solutions of these derivatives have the necessary characteristics for use in viscosurgery, particularly ophthalmic viscosurgery. These characteristics are a physiological osmolarity in the order of 250-350 mM and a pH between 5.5 and 7.5. Also provided is the combined use of these solutions mixed with other materials usable in viscosurgery such as hyaluronic acid, chondroitin sulfate and carboxymethylcellulose. However, such mixtures are not formed and neither is the known problem of mutual compatibility between the anionic and cationic polymers mentioned. Consequently the conditions needed for said mixtures do not generate coacervates or possible phase separations, with irreversible loss of the condition for a molecularly dispersed solution of the mixtures and with modifications of the reheological characteristics of the compositions, are missing WO Patent 2005/061611 (White, B. J. et al.) describes the preparation of hydrogels consisting of a composition comprising water soluble crosslinked derivatives of a basic polysaccharide and a non-crosslinked anionic polysaccharide. In particular said hydrogels are obtained by mixing hyaluronic acid with crosslinked N-carboxymethyl, O-carboxymethyl, O-hydroxyethyl chitosan derivatives or with partially acetylated chitosans. These chitosan derivatives can be mixed in solution with hyaluronic acid as, according to the inventors, they are solubilized under pH conditions such as not to have any positive charges on the chain and to avoid formation of ionic complexes. In this manner coacervation with the polyanion is prevented by the complete removal or compensation of charge on one of the polymers. These are therefore solutions of polyanion/neutral polysaccharide or polyanion/polyampholyte.

However, the feasibility of using low or relatively low molecular weight polysaccharides, even those of different charges mixed together, to obtain compositions with suitable physico-chemical features is an aim still to be pursued in view of the great applicative interest and the plurality of applications in, inter alia, the biomedical field, for high viscosity/viscoelasticity polysaccharide solutions. In this respect, new technical solutions for preparing polysaccharide solutions having physico-chemical characteristics suitable for the numerous known applications thereof are still being actively searched.

Therefore a first purpose of the present invention is the preparation of aqueous polysaccharide solutions with a suitable viscosity/viscoelasticity for application at least in viscosupplementation treatment of inflammatory and traumatic articular pathologies, without excluding other known applications for said viscous and/or viscoelastic solutions in the biomedical field such as ophthalmic surgery.

A second purpose is the preparation of said compositions with commercially available and inexpensive polysaccharides, and therefore of low or relatively low average molecular weight, without having to subject said polysaccharides to complex chemical manipulations which, while improving their physico-chemical characteristics, have a significant impact on costs.

SUMMARY

For the fullfillment of the aforementioned purposes the Inventors have identified suitable derivatives of basic polysaccharides which when physically mixed with anionic polysaccharides, provide, under suitable conditions, aqueous solutions of both polysaccharides without generating insoluble coacervates.

The objects pursued are achieved with anionic polysaccharides and oligosaccharide derivatives of chitosan. Furthermore, the identified conditions can generally be applied to obtain soluble mixtures of modified polycationic polyaccharides and polyanionic polysaccharides.

Surprisingly, as well as giving rise to compositions in which said physical mixtures of polyanionic polysaccharides and polycationic polysaccharide derivatives are soluble in an aqueous environment, said compositions show a considerable increase in the viscosity of the polyanion solution following addition of the oligosaccharide derivatives of chitosan.

The invention therefore provides polysaccharide compositions comprising aqueous solutions of mixtures of at least one anionic polysaccharide and at least one oligosaccharide derivative of chitosan, wherein said chitosan derivatives have a degree of derivatization of at least 40% and wherein said aqueous solutions have an ionic strength of at least 50 mM and not greater than 175 mM, and a pH of at least 7.

The invention also provides the use of said compositions of polysaccharide mixtures in the biomedical field, including their use in intra-articular viscosupplementation for treatment of osteoarticular pathologies and in ophthalmic surgery.

DETAILED DESCRIPTION OF THE INVENTION

Figure 1:
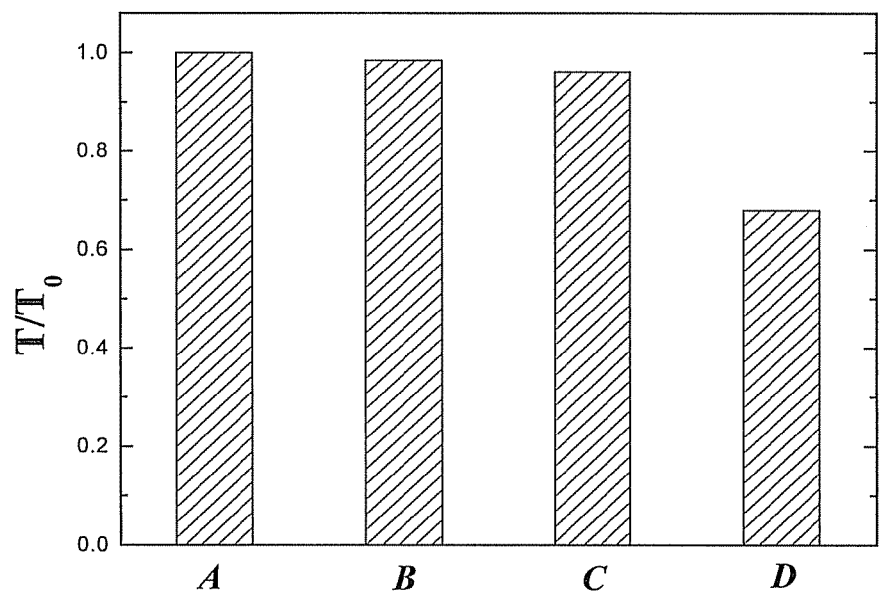
FIG. 1: Relationship between transmittance ($\lambda=600$ nm) of solutions containing hyaluronic acid and chitosan modified with lactose (hereinafter named briefly chitlac) and that of the individual polymers ($T_0$) under the following conditions A) (ex. 4) NaCl 0.15 M Hepes 10 mM pH 7.4; B) (ex. 5) NaCl 0.1 M, Hepes 10 mM, pH 7.4; C) (ex. 6) NaCl 0.05 M, Hepes 10 mM, pH 7.4; D) (ex. 7) NaCl 0.025 M, Hepes 10 mM, pH 7.4. Total polymer concentration: 2%. Weight ratio of hyaluronic acid to chitlac=3:1. In all solutions the osmolarity value was maintained at 300 mM by addition of the non-ionic solute mannitol. Measurements were undertaken by means of a CaryE4 UV-visible spectrophotometer at a temperature of 25° C.

The purposes and advantages of the polysaccharide compositions of the present invention will be better understood from the following detailed description where, by way of non-limiting illustration of the invention, some examples of compositions and their physico-chemical characterization will be described.

With the aim of obtaining compositions of polyanionic polysaccharides, such as for example hyaluronic acid, soluble in an aqueous environment, with a viscosity and/or viscoelasticity suitable for the numerous known uses of the polysaccharides, in particular but non exclusively for articular viscosupplementation, and starting from non-high average molecular weight polysaccharides but without their undergoing complex chemical manipulations, the Inventors have found that a possible solution was achievable by using oligosaccharide derivatives of chitosan.

This aim is achievable with compositions comprising mixtures of acidic polysaccharides and derivatives of basic polysaccharides, i.e. polysaccharide compositions comprising aqueous solutions of mixtures of at least one anionic polysaccharide and at least one oligosaccharide derivative of chitosan, wherein said polycationic polysaccharide derivatives have a degree of derivatization of at least 40% and wherein said aqueous solutions have an ionic strength of at least 50 mM and not greater than 175 mM, and a pH of at least 7. In order to obtain the aqueous solutions of polysaccharide mixtures of the invention, the anionic polysaccharides and chitosan derivatives are within a polyanion to oligosaccharide derivative weight ratio range comprised from 10:1 (polyanion:chitosan derivative) to 1:1. For the purposes of the present invention the preferred weight ratios between the polysaccharides are in particular within a range from 3:1 to 1:1, while the polymer concentration of the solutions is between 1.5% w/v (g/mL) and 3% w/v (g/mL).

Derivatisation of chitosan with saccharide side groups, for example by inserting lactose units via a reductive amination reaction, is known and reported in the previously mentioned U.S. Pat. No. 4,424,346; also known is that said derivatisation allows a greater solubility of this basic polysaccharide in water. Chitosan, as known by an expert in the field, can be derivatised by reductive amination with reducing oligosaccharides containing from 1 to 4 glycosidic units. In particular for the purposes of the present invention said oligosaccharides comprise from 2 to 4 glycosidic units and the same are preferably selected from the group consisting of lactose, cellobiose, cellotriose, maltose, maltotriose, maltotetraose, chitobiose, chitotriose, melibiose.

The average molecular weight (hereinafter indicated as $M_w$) of the chitosan usable for producing the aforementioned oligosaccharide derivatives can be up to 1,500 kDa, being preferably within the range from 400 kDa to 1,000 kDa. In addition, for the purposes of the present invention the degree of substitution of the chitosan amine groups with said oligosaccharides has to be above 40-45% (~45%). Preferably, the degree of substitution of the chitosan amine groups with oligosaccharide can be within the range from 50% to 80%, being more preferably 70%.

The preparation process of said oligosaccharide derivatives of chitosan is a known process and comprises treating a solution of chitosan in acetic acid (pH 4.5) and methanol with a reducing saccharide, such as lactose, in the presence of sodium cyanoborohydride. The interaction between chitosan amine groups and the lactose aldehyde group leads to the formation of an unstable intermediate known as a Schiff base. This is reduced in the presence of borohydride leading to the formation of a stable secondary amine.

With regard to the polyanionic polysaccharides, the compositions of polysaccharide mixtures of the invention can be obtained with carboxylated anionic polysaccharides (e.g. hyaluronic acid, alginates, pectins, carboxymethylcellulose, xanthan and other microbial carboxylated polysaccharides) and sulfates (carrageenans, agarose sulfate, keratan sulfate, dermatan sulfate, sulfated starch, heparin, heparan sulfate). For the compositions of the invention the acidic polysaccharides are preferably selected from the group consisting of hyaluronic acid, alginates, pectins, carboxymethylcellulose for the carboxylates and carrageenans, agarose sulfate for the sulfates. The average molecular weight ($M_w$) of the polyanions can reach 1,500 kDa and preferably be from 100 kDa to 1,000 kDa; more preferably, average molecular weights of about 900 kDa are utilized.

For the purposes of the present invention the chitosan-derivative and polyanion mixtures can have a total polymer concentration up to 3% w/v (g/mL). Preferably said total polymer concentrations are within the range from 1.5% w/v (g/mL) to 3% w/v (g/mL).

In general the compatibility of the two different polymers in solution is made possible at pH 7.4 in the presence of a supporting salt able to produce an ionic strength of at least 50 mM for ratios preferably from 10:1 (polyanion:chitosan derivative) to 1:1 (polyanion:chitosan derivative) and more preferably from 3:1 (polyanion:chitosan derivative) to 1:1 (polyanion:chitosan derivative).

Therefore, according to the invention the conditions to be applied for mixing the two polymer solutions, so that said mixtures form a solution in water, are pH values from 7 to 8 and preferably around the physiological pH 7.4 and a suitable ionic strength. In particular for the purposes of obtaining an adequate ionic strength [ionic strength=½($\Sigma_i c_i z_i^2$) in which $c_i$ is the concentration of the $i^{th}$ ionic species and $z_1$ is the absolute value of its electrical charge], the compositions comprising the mixtures of the invention contain a concentration of a simple supporting salt, preferably NaCl, of between 0.05 M (ionic strength=50 mM) and 0.175 M (ionic strength=175 mM) when the total polymer concentration is between 1.5% and 3%. Preferably, the supporting salt concentration is 0.15 M (ionic strength=150 mM) for a solution containing a total polymer concentration up to 3%. As well as the solution of supporting salt and polysaccharides, a small quantity of buffer can be added. Preferably, Hepes ((N-(2-hydroxyethyl) piperazine-N'-(2-ethanesulfonic acid) sodium salt) at a concentration of 10 mM is added to the system to maintain system pH at a constant value, preferably between 7 and 8, even more preferably at 7.4.

In addition, for the biomedical uses of said compositions an osmolarity value between 250 and 350 mM must be ensured for the aqueous solutions of the polysaccharide mixtures of the invention, by means of a possible further addition of non-ionic solutes. Preferred of the usable non-ionic solutes is mannitol.

The synthesis of some oligosaccharide derivatives of chitosan and examples for preparing compositions comprising mixtures of polysaccharides of the invention are described hereinafter by way of non-limiting illustration.

Example 1

Synthesis of Lactose Derivatives of Chitosan (Named Chitlac)

Chitosan (1.5 g, degree of acetylation 11%) is dissolved in 110 mL of a solution of methanol (55 mL) and 1% acetic acid buffer at pH 4.5 (55 mL). 60 mL of a solution of methanol (30 mL) and 1% acetic acid buffer at pH 4.5 (30 mL) containing lactose (2.2 g) and sodium cyanoborohydride (900 mg) are added. The mixture is left under agitation for 24 hours, transferred into dialysis tubes (cut off: 12000 Da) and dialyzed against 0.1 M NaCl (2 changes) and against deionised water until the conductivity is 4 µS at 4° C. Finally, the solution is filtered through Millipore 0.45 µm filters and lyophilized.

Example 2

Synthesis of Cellobiose Derivatives of Chitosan (Hereinafter Named Chitcell)

Chitosan (1.5 g, degree of acetylation 11%) is dissolved in 110 mL of a solution of methanol (55 mL) and 1% acetic acid buffer at pH 4.5 (55 mL). 60 mL of a solution of methanol (30 mL) and 1% acetic acid buffer at pH 4.5 (30 mL) containing cellobiose (2.2 g) and sodium cyanoborohydride (900 mg) are added. The mixture is left under agitation for 24 hours, transferred into dialysis tubes (cut off: 12000 Da) and dialyzed against NaCl 0.1 M (2 changes) and against deionised water until the conductivity is 4 μS at 4° C. Finally, the solution is filtered through Millipore 0.45 μm filters and lyophilized.

Example 3

Synthesis of Maltotriose Derivatives of Chitosan (Hereinafter Named Chitmal3)

Chitosan (300 mg, degree of acetylation 11%) is dissolved in 22 mL of a solution of methanol (11 mL) and 1% acetic acid buffer at pH 4.5 (11 mL). 12 mL of a solution of methanol (6 mL) and 1% acetic acid buffer at pH 4.5 (6 mL) containing maltotriose (650 mg) and sodium cyanoborohydride (180 mg) are added. The mixture is left under agitation for 24 hours, transferred into dialysis tubes (cut off: 12000 Da) and dialyzed against NaCl 0.1 M (2 changes) and against deionised water until the conductivity is 4 μS at 4° C. Finally, the solution is filtered through Millipore 0.45 μm filters and lyophilized.

The examples of polysaccharide mixtures described hereinafter are obtained with the aforesaid chitosan derivatives and commercial polyanionic polysaccharides of various average molecular weights.

Example 4

3:1 w/w Mixture of Low $M_w$ Hyaluronic Acid:Chitlac; Total Polysaccharide Concentration 2% w/v (g/mL)

20 ML of a solution of hyaluronic acid (600 mg, $M_w$~160,000) containing NaCl 0.15 M, Hepes 10 mM at pH 7.4 are prepared. 20 mL of a chitlac (200 mg, $M_w$~1.5×10$^6$ of ex. 1) solution containing NaCl 0.15 M, Hepes 10 mM at pH 7.4 are prepared. The two solutions are mixed by a magnetic rod stirrer to obtain 40 mL of a solution containing 1.5% of hyaluronic acid and 0.5% of chitlac (total polymer concentration 2%), completely transparent and without precipitates and/or coacervates.

Example 5

3:1 w/w Mixture of Low $M_w$ Hyaluronic Acid:Chitlac; Total Polysaccharide Concentration 2% w/v (g/mL)

20 mL of a solution of hyaluronic acid (600 mg, $M_w$~160,000) containing NaCl 0.1 M, Hepes 10 mM at pH 7.4 are prepared. 20 mL of a chitlac (200 mg, $M_w$~1.5×10$^6$ of ex. 1) solution containing NaCl 0.1 M, Hepes 10 mM at pH 7.4 are prepared. The two solutions are mixed by a magnetic rod stirrer to obtain 40 mL of a solution containing 1.5% of hyaluronic acid and 0.5% of chitlac (total polymer concentration 2%), completely transparent and without precipitates and/or coacervates.

Example 6

3:1 w/w Mixture of Low $M_w$ Hyaluronic Acid:Chitlac; Total Polysaccharide Concentration 2% w/v (g/mL)

20 mL of a solution of hyaluronic acid (600 mg, $M_w$~160,000) containing NaCl 0.05 M, Hepes 10 mM at pH 7.4 are prepared. 20 mL of a chitlac (200 mg, $M_w$~1.5×10$^6$ of ex. 1) solution containing NaCl 0.05 M, Hepes 10 mM at pH 7.4 are prepared. The two solutions are mixed by a magnetic stirrer to obtain 40 mL of a solution containing 1.5% of hyaluronic acid and 0.5% of chitlac (total polymer concentration 2%), completely transparent and without precipitates and/or coacervates.

Example 7

3:1 w/w Mixture of Low $M_w$ Hyaluronic Acid:Chitlac; Total Polysaccharide Concentration 2% w/v (g/mL)

20 mL of a solution of hyaluronic acid (600 mg, $M_w$~160,000) containing NaCl 0.025 M, Hepes 10 mM at pH 7.4 are prepared. 20 mL of a chitlac (200 mg, $M_w$~1.5×10$^6$ of ex. 1) solution containing NaCl 0.025 M, Hepes 10 mM at pH 7.4 are prepared. The two solutions are mixed by a magnetic stirrer to obtain 40 mL of a solution containing 1.5% of hyaluronic acid and 0.5% of chitlac (total polymer concentration 2%), where the presence of coacervates is observed.

Example 8

1:1 w/w Mixture of Low $M_w$ Hyaluronic Acid:Chitlac; Total Polysaccharide Concentration 1.5% w/v (g/mL)

20 mL of a solution of hyaluronic acid (300 mg, $M_w$~160,000) containing NaCl 0.15 M, Hepes 10 mM at pH 7.4 are prepared. 20 mL of a chitlac (300 mg, $M_w$~1.5×10$^6$ of ex. 1) solution containing NaCl 0.15 M, Hepes 10 mM at pH 7.4 are prepared. The two solutions are mixed by a magnetic stirrer to obtain 40 mL of a solution containing 0.75% of hyaluronic acid and 0.75% of chitlac (total polymer concentration 1.5%), completely transparent and without precipitates and/or coacervates.

Example 9

1:1 w/w Mixture of Carboxymethylcellulose:Chitlac; Total Polysaccharide Concentration 1.5% w/v (g/mL)

20 mL of a solution of carboxymethylcellulose (300 mg, $M_w$~270,000, d.s. 0.9) containing NaCl 0.15 M, Hepes 10 mM at pH 7.4 are prepared. 20 mL of a chitlac (300 mg, $M_w$~1.5×10$^6$ of ex. 1) solution containing NaCl 0.15 M, Hepes 10 mM at pH 7.4 are prepared. The two solutions are mixed by a magnetic stirrer to obtain 40 mL of a solution containing 0.75% of carboxymethylcellulose and 0.75% of chitlac (total polymer concentration 1.5%), completely transparent and without precipitates and/or coacervates.

Example 10

1:1 w/w Mixture of Alginate:Chitlac; Total Polysaccharide Concentration 1.5% w/v (g/mL)

20 mL of a solution of alginate (300 mg, $M_w$~130,000) containing NaCl 0.15 M, Hepes 10 mM at pH 7.4 are prepared. 20 mL of a chitlac (300 mg, $M_w$~1.5×10$^6$ of ex. 1) solution containing NaCl 0.15 M, Hepes 10 mM at pH 7.4 are prepared. The two solutions are mixed by a magnetic stirrer to obtain 40 mL of a solution containing 0.75% of alginate and 0.75% of chitlac (total polymer concentration 1.5%), completely transparent and without precipitates and/or coacervates.

Example 11

1:1 w/w Mixture of Agarose Sulfate:Chitlac; Total Polysaccharide Concentration 1.5% w/v (g/mL)

20 mL of a solution of agarose sulfate (300 mg, low gelling point) containing NaCl 0.15 M, Hepes 10 mM at pH 7.4 are prepared at a temperature above the gel melting point. 20 mL of a chitlac (300 mg, $M_w \sim 1.5 \times 10^6$ of ex. 1) solution containing NaCl 0.15 M, Hepes 10 mM at pH 7.4 are prepared and maintained at the same temperature as the previous solution. The two solutions are mixed under hot conditions (~50° C.) by a magnetic stirrer to obtain 40 mL of a solution containing 0.75% of agarose sulfate and 0.75% of chitlac (total polymer concentration 1.5%), completely transparent and without precipitates and/or coacervates.

Example 12

1:1 w/w Mixture of κ-Carrageenan:Chitlac; Total Polysaccharide Concentration 1.5% w/v (g/mL)

20 mL of a solution of κ-carrageenan (300 mg, $M_w \sim 270,000$) containing NaCl 0.15 M, Hepes 10 mM at pH 7.4 are prepared. 20 mL of a chitlac (300 mg, $M_w \sim 1.5 \times 10^6$ of ex. 1) solution containing NaCl 0.15 M, Hepes 10 mM at pH 7.4 are prepared. The two solutions are mixed by a magnetic stirrer to obtain 40 mL of a solution containing 0.75% of κ-carrageenan and 0.75% of chitlac (total polymer concentration 1.5%) without precipitates.

Example 13

1:1 w/w Mixture of Low $M_w$ Hyaluronic Acid:Chitlac; Total Polysaccharide Concentration 1.5% w/v (g/mL) in Deionised Water 20 mL of a solution of hyaluronic acid (300 mg, $M_w \sim 160,000$) in deionised water are prepared. 20 mL of a chitlac (300 mg, $M_w \sim 1.5 \times 10^6$ of ex. 1) solution in deionised water are prepared. The two solutions are mixed by a magnetic stirrer to obtain 40 mL of a mixture containing 0.75% of hyaluronic acid and 0.75% of chitlac (total polymer concentration 1.5%) where the formation of coacervates/precipitates between the two polysaccharides is observed.

Example 14

1:1 w/w Mixture of Low $M_w$ Hyaluronic Acid:Chitlac; Total Polysaccharide Concentration 1.5% w/v (g/mL) at pH 7.4 without Supporting Salt 20 mL of a solution of hyaluronic acid (300 mg, $M_w \sim 160,000$) containing Hepes 10 mM at pH 7.4 are prepared. 20 mL of a chitlac (300 mg, $M_w \sim 1.5 \times 10^6$ of ex. 1) solution containing Hepes 10 mM at pH 7.4 are prepared. The two solutions are mixed by a magnetic stirrer to obtain 40 mL of a mixture containing 0.75% of hyaluronic acid and 0.75% of chitlac (total polymer concentration 1.5%) where the formation of coacervates/precipitates between the two polysaccharides is observed.

Example 15

1:1 w/w Mixture of Low $M_w$ Hyaluronic Acid: Poly-L-Lysine (PLL); Total Polysaccharide Concentration 1.5% w/v (g/mL)

20 mL of a solution of hyaluronic acid (300 mg, $M_w \sim 160,000$) containing NaCl 0.15 M, Hepes 10 mM at pH 7.4 are prepared. 20 mL of a poly-L-lysine (PLL) (300 mg, $M_w \sim 20,000$) solution containing NaCl 0.15 M, Hepes 10 mM at pH 7.4 are prepared. The two solutions are mixed by a magnetic stirrer to obtain 40 mL of a mixture containing 0.75% of hyaluronic acid and 0.75% of PLL (total polymer concentration 1.5%) where the formation of coacervates/precipitates between the two polysaccharides is observed.

Example 16

Labelling the Alginate with Rhodamine

A quantity of 123 Rhodamine sufficient to label 1 uronic group of the alginate in about every 1500, is added to a solution of alginate (300 mg, $M_w \sim 130,000$) in a morpholinoethane sulfonic acid (MES, 100 mL) buffer containing 10% ethanol, N-hydroxysuccinimide (NHS) and 1-ethyl-2-[3-(dimethylamino)propyl]carbodiimide (EDC) (molar ratio of [EDC]/[URAlginate]=1.5; molar ratio of [NHS]/[EDC]=1). The solution is maintained under agitation in darkness for 24 hours, dialyzed against $NaHCO_3$ 0.05 M (3 changes) and against deionized water until conductivity is 4 µS at 4° C. Finally, the solution is filtered through 0.45 µm Millipore filters and lyophilized.

Example 17

Labelling Chitlac with Fluorescein

A quantity of fluorescein isothiocyanate sufficient to modify one amine group in about every 2000 is added to a solution of chitlac (200 mg, $M_w \sim 1.5 \times 10^6$ of ex. 1) in $NaHCO_3$ 0.5 M (65 mL). The solution is maintained under agitation in darkness for 24 hours, dialyzed against $NaHCO_3$ 0.05 M (3 changes) and against deionized water until conductivity is 4 µS at 4° C. Finally, the solution is filtered through 0.45 µm Millipore filters and lyophilized.

Example 18

1:1 w/w Mixture of Alginate:Chitlac; Total Polysaccharide Concentration 0.15% w/v (g/mL)

10 mL of a solution of rhodamine-labelled alginate (15 mg, $M_w \sim 130,000$ of ex. 16) containing NaCl 0.015 M, Hepes 1 mM at pH 7.4 are prepared. 10 mL of a solution of fluorescein-labelled chitlac (15 m mg, $M_w \sim 1.5 \times 10^6$ of ex. 17) containing NaCl 0.015 M, Hepes 1 mM at pH 7.4 are prepared. The two solutions are mixed by a magnetic stirrer to obtain 20 mL of a solution containing 0.075% of rhodamine-labelled alginate and 0.075% of fluorescein-labelled chitlac (total polymer concentration 0.15%), completely transparent and without precipitates and/or coacervates.

Example 19

3:1 w/w Mixture of High $M_w$ Hyaluronic Acid:Chitlac; Total Polysaccharide Concentration 2% w/v (g/mL)

20 mL of a solution of hyaluronic acid (600 mg, $M_w$ about $8-9 \times 10^5$) containing NaCl 0.15 M, Hepes 10 mM at pH 7.4 are prepared. 20 mL of a solution of chitlac (200 mg, $M_w \sim 1.5 \times 10^6$ of ex. 1) containing NaCl 0.15 M, Hepes 10 mM at pH 7.4 are prepared. The two solutions are mixed by a magnetic stirrer to obtain 40 mL of a solution containing 1.5% of hyaluronic acid and 0.5% of chitlac (total polymer concentration 2%), completely transparent and without precipitates and/or coacervates.

Example 20

3:1 w/w Mixture of Alginate:Chitlac; Total Polysaccharide Concentration 2% w/v (g/mL)

20 mL of a solution of alginate (600 mg, $M_w \sim 130{,}000$) containing NaCl 0.15 M, Hepes 10 mM at pH 7.4 are prepared. 20 mL of a solution of chitlac (200 mg, $M_w \sim 1.5 \times 10^6$ of ex. 1) containing NaCl 0.15 M, Hepes 10 mM at pH 7.4 are prepared. The two solutions are mixed by a magnetic stirrer to obtain 40 mL of a solution containing 1.5% of alginate and 0.5% of chitlac (total polymer concentration 2%), completely transparent and without precipitates and/or coacervates.

Example 21

1:1 w/w Mixture of Hyaluronic Acid:Chitlac; Total Polysaccharide Concentration 3% w/v (g/mL)

20 mL of a solution of hyaluronic acid (600 mg, $M_w \sim 240{,}000$) containing NaCl 0.15 M, Hepes 10 mM at pH 7.4 are prepared. 20 mL of a solution of chitlac (600 mg, $M_w \sim 1.5 \times 10^6$ of ex. 1) containing NaCl 0.15 M, Hepes 10 mM at pH 7.4 are lo prepared. The two solutions are mixed by a magnetic stirrer to obtain 40 mL of a solution containing 1.5% of hyaluronic acid and 1.5% of chitlac (total polymer concentration 3%), completely transparent and without precipitates and/or coacervates.

Example 22

1:1 w/w Mixture of Hyaluronic Acid:Chitosan Derivatives (Chitlac; Chitcell; Chitmal3)

20 mL of a solution of hyaluronic acid (300 mg, $M_w \sim 160{,}000$) containing NaCl 0.15 M, Hepes 10 mM at pH 7.4 are prepared. 20 mL of a solution of chitlac (300 mg, $M_w 1.5 \times 10^6$ of ex. 1) containing NaCl 0.15 M, Hepes 10 mM at pH 7.4 are prepared. The two solutions are mixed by a magnetic stirrer to obtain 40 mL of a solution containing 0.75% of hyaluronic acid and 0.75% of chitlac (total polymer concentration 1.5%), completely transparent and without precipitates and/or coacervates.

Using the same method, mixtures of hyaluronic acid with chitcell (ex. 2) and hyaluronic acid with chitmal3 (ex. 3) were also prepared, to obtain 40 mL of solutions containing 0.75% of hyaluronic acid and 0.75% of chitcell or chitmal3 (total polysaccharide concentration 1.5%), completely transparent and without precipitates and/or coacervates.

Figure 2:
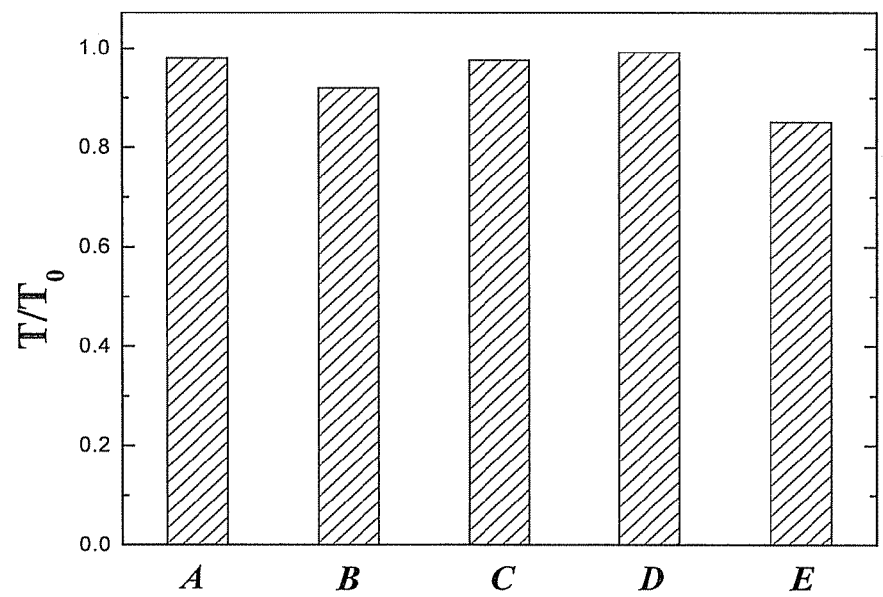
FIG. 2: Relationship between transmittance (λ=600 nm) of binary polysaccharide mixtures (chitlac/polyanions) and that of the individual polymers ($T_0$) for the following biopolymers: A) (ex. 8) Hyaluronic acid; B) (ex. 9) Carboxymethylcellulose; C) (ex. 10) Alginate; D) (ex. 11) Agarose sulfate; E) (ex. 12) Carrageenan. Conditions: NaCl 0.15 M, Hepes 10 mM, pH 7.4. Total polymer concentration: 1.5%. Weight ratio of polyanions to chitlac=1:1. In the case of D) (ex. 11) mixing was undertaken at about 50° C. Measurements were carried out as previously described in FIG. 1.
Figure 3:
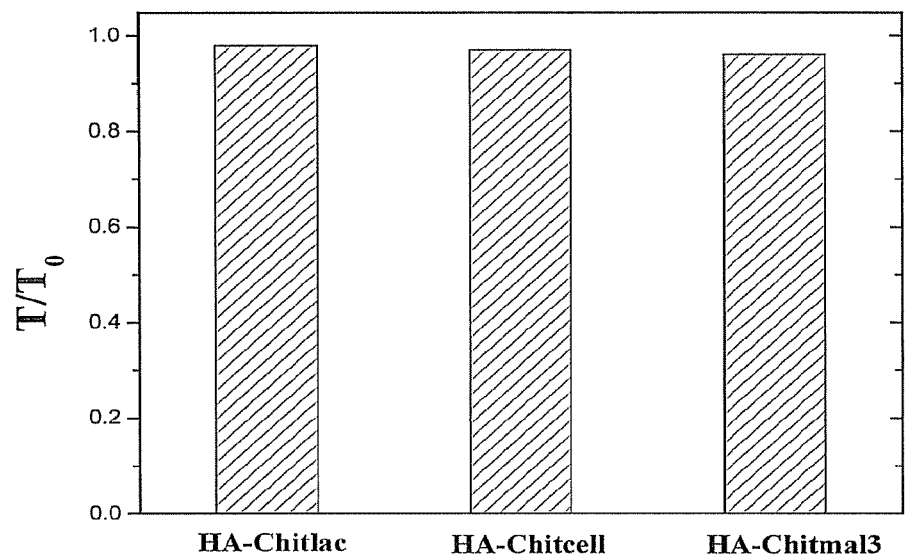
FIG. 3: Relationship between transmittance (λ=600 nm) of binary polysaccharide mixtures (hyaluronic acid/chitosan derivatives of examples 1, 2 and 3) and that of the individual polymers ($T_0$) for the following derivatives: Chitlac (chitosan modified with lactose by reductive amination; ex. 1); Chitcell (chitosan modified with cellobiose by reductive amination; ex. 2); Chitmal3 (chitosan modified with maltotriose by reductive amination; ex. 3). Conditions: NaCl 0.15 M, Hepes 10 mM, pH 7.4. Total polymer concentration: 1.5%. Weight ratio of hyaluronic acid to modified chitosans=1:1. Measurements were carried out as previously described in FIG. 1.
Figure 3A:
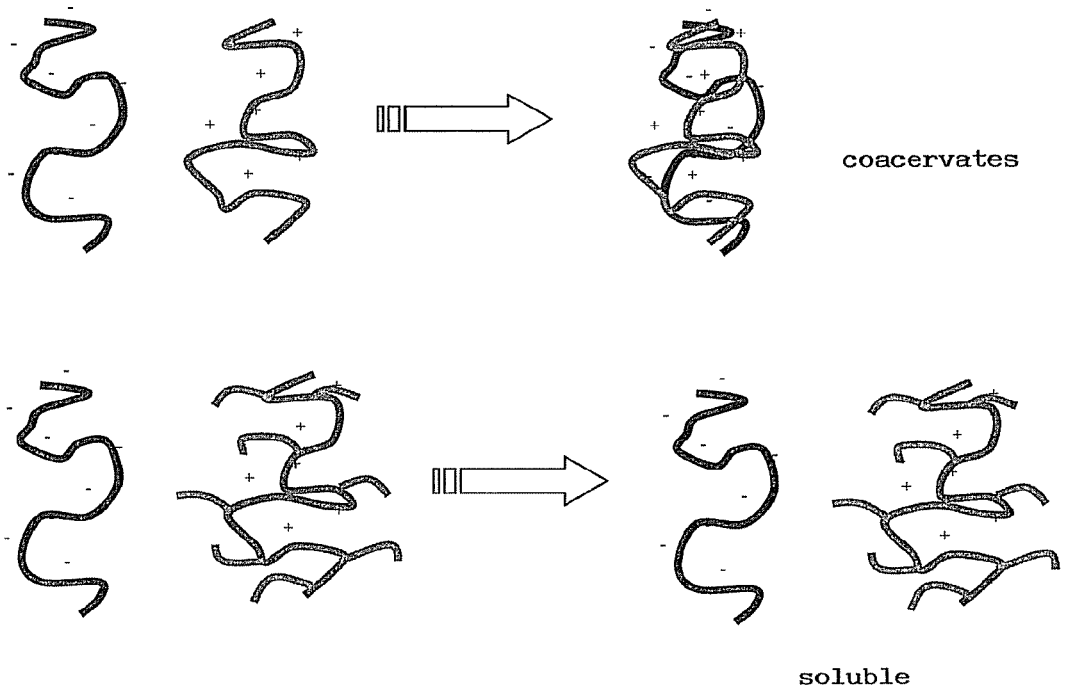
FIG. 3A: The scheme illustrates the formation of coacervates between polyanions and polycations or of their soluble solutions.

Physico-Chemical Characterization of the Polysaccharide Mixtures of Examples 4 to 22 Compared with the Single Anionic Polysaccharide and Chitosan Derivative Components a) Influence of Ionic Strength on Polysaccharide Mixture Solubility To evaluate the effect induced by ionic strength variation on the solubility of the polysaccharide mixtures of the invention, the transmittance ratio (T) at $\lambda=600$ nm was measured of solutions containing hyaluronic acid and a chitosan derivative (chitlac), prepared as in examples 4 to 7 described above. FIG. 1 highlights the fact that the aqueous solubility of the mixture of polyanions and modified chitosan is ensured, in the presence for example of a total polymer concentration of 2%, and with a supporting salt concentration above or equal to 0.05M. In particular, the figure gives the ratio of transmittance (measured at 600 nm) of a binary polymer solution to that of the separate polysaccharides. A transmittance equal to or approaching 1 indicates an absence of coacervates or precipitates in the binary polymer solution. In contrast, when the salt in the mixture is reduced to a value of less than 0.05M, coacervate formation is observed with consequent significant reduction in transmittance.

b) Mixtures of Different Anionic Polysaccharides and a Chitosan Derivative (Chitlac) in 1:1 w/w Ratios To evaluate the effect induced by varying anionic polysaccharide type on the solubility of the mixtures containing oligosaccharide-modified chitosan of the invention, the ratio of transmittance (T) at $\lambda=600$ nm was measured as before of solutions containing anionic polysaccharides selected from hyaluronic acid, carboxymethylcellulose, alginate, agarose sulfate and carrageenan and a chitosan derivative (chitlac) prepared as in examples 8 to 12 described above, at a high w/w ratio i.e. 1:1. FIG. 2 shows that the solubility of the polysaccharide mixtures is ensured even when the weight ratio of the two polymers is 1:1 with a total polymer concentration of 1.5%. Mixing can also be achieved by maintaining system solubility with different polyanions, either carboxylated or sulfated.

c) Mixtures of Polyanionic Polysaccharides and Chitosan Derivatives (Chitlac; Chitcell; Chitmal3) in 1:1 w/w Ratios The solubility of the polysaccharide compositions of the invention, measured as before, proves not to be influenced by the various derivatisations of chitosan, as the binary mixtures prepared as in example 22 show equal $T/T_0$ values. In this respect, FIG. 3 demonstrates how the ability to prepare polymer solutions with polyanions and oligosaccharide-modified chitosan does not depend on the chemical nature of this latter. By substituting cellobiose (chitcell) or maltotriose (chitmal3), respectively a disaccharide and a trisaccharide, for lactose (chitlac), there is no significant formation of coacervates.

The feasibility of mixing polyanions with the oligosaccharide derivatives of chitosan to obtain a solution, under suitable conditions, is essentially due to three factors. The first is steric hindrance caused by the oligosaccharide side chains having been introduced into the cationic polysaccharide. These interfere with the approach of the anionic polysaccharide and prevent the coupling of the two polymer systems over long tracts of the chains. This effect is illustrated in scheme 1.

Figure 4:
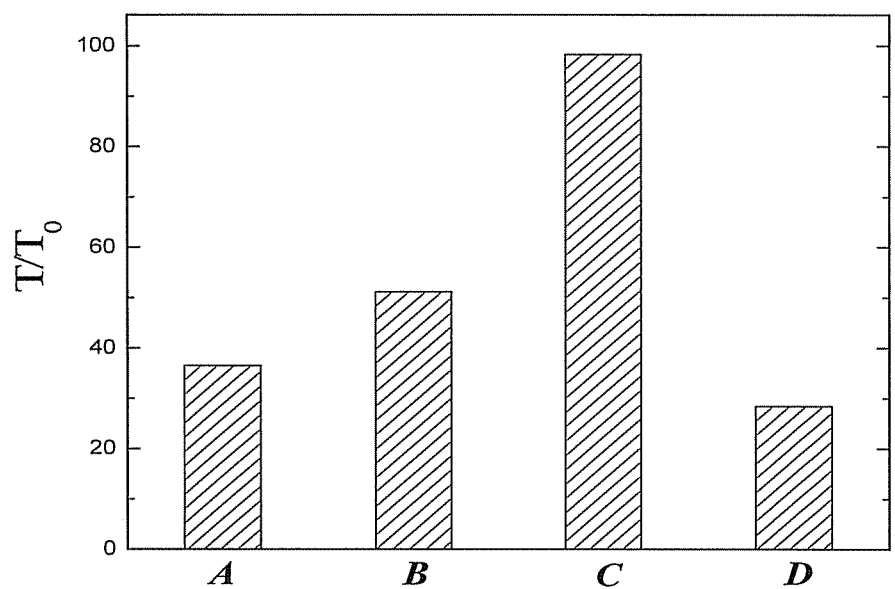
FIG. 4: Relationship between transmittance (λ=600 nm) of binary polysaccharide mixtures and that of the individual polymers ($T_0$) under the following conditions: A) (ex. 13) hyaluronic acid/chitlac in deionised water (pH~5.5); B) (ex. 14) hyaluronic acid/chitlac in Hepes 10 mM, pH 7.4; C) (ex. 8) hyaluronic acid/chitlac in NaCl 0.15M, Hepes 10 mM, pH7.4; D) (ex. 15) hyaluronic acid/poly-L-lysine (PLL) in NaCl 0.15M, Hepes 10 mM, pH7.4; Total polymer concentration: 1.5%. Weight ratio of hyaluronic acid to polycation=1:1. Measurements were carried out as previously described in FIG. 1.

In addition, the use of a physiological pH, preferably pH 7.4, allows a reduction in the charge on the cationic polysaccharide, chitlac, which maintains good water solubility by virtue of the saccharide side chains. Finally, the presence of a supporting salt, preferably sodium chloride, enables the charges on the two polymers to be shielded hence limiting the electrostatic interactions between the two polymers so as to avoid coacervation/precipitation. By combining these three factors, solutions of polyanions/oligosaccharide-modified chitosan can be obtained. In this respect, as deduced from FIG. 4, the formation of polymer mixtures of hyaluronic acid and chitlac in deionised water (pH~5.5) is not feasible, despite the presence of said steric factors. Neither does the use of physiological pH (7.4) without the presence of a supporting salt result in a true solution being obtained. Finally, the use of a polycation different from chitlac, for example poly-L-lysine (PLL) which is soluble at a physiological pH in the presence of a supporting salt, does not enable solutions to be obtained if polyanions are present (FIG. 4).

Figure 5:
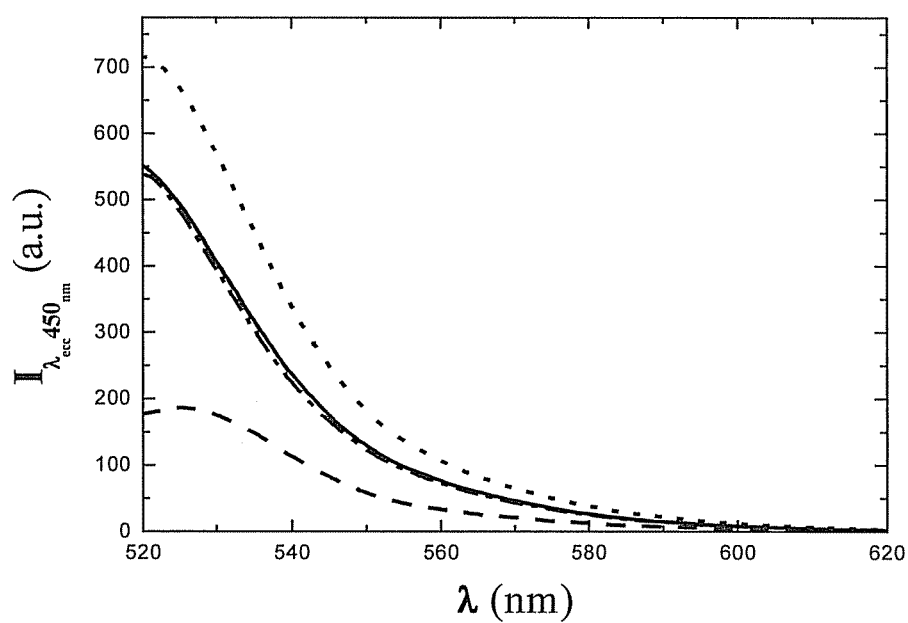
FIG. 5: Emission spectra of (— —) alginate labelled with rhodamine (ex. 16) (0.75 g/L) and (•—•) chitlac labelled with fluorescein (ex. 17) (0.75 g/L) compared with (•••) the theoretical sum of the two contributions, and (—) the spectrum of the mixture of rhodamine-labelled alginate and fluorescein-labelled chitlac (ex. 18) (total polymer concentration 0.15 g/L, mass ratio of the two polysaccharides=1:1. Conditions: NaCl 0.15 M, Hepes 1 mM, pH 7.4). Excitation wavelength 450 nm. Instrumental set-up: scan rate 50 nm/min, emission slit 4.5 nm, excitation slit 4.5 nm. Measurements were carried out by means of a Perkin Elmer LS 50B fluorescence spectrometer at a temperature of 25° C.

The absence of coacervate formation, however, does not mean that there are no interactions between the positive charges on the polycation, for example chitlac, and the negative ones on the polyanion, for example hyaluronic acid or alginate. On the contrary, a FRET (Fluorescence Resonance Energy Transfer) experiment shows the existence of these essentially electrostatic (coulomb) interactions (FIG. 5). In this experiment, the polyanion (alginate) was labelled with rhodamine and the polycation (chitlac) with fluorescein. If it is assumed that mixing takes place without interactions between opposing charges on the two polysaccharides, the intensity of the fluorescence emission spectrum of the mixture corresponds to the sum of the intensities of the two spectra recorded separately. If, conversely, the spectrum of the binary solution of anionic and cationic polysaccharides is found to be lower than the sum of the spectra of the two polymers taken separately, this indicates the establishment of strong short range interactions (on a length scale in the order of 5 nm) between the two polymers (fluorescence quenching). Typically the ionic interactions fall within this distance. FIG. 5 shows that the emission spectrum of the binary solution of alginate and chitlac has a lower intensity than the sum of the emission spectra intensities of the two polymers tested separately, indicating the presence of ionic interactions between the positive charges of chitlac and the negative ones of alginate. In this sense, the compositions of the invention enable solutions with anionic and cationic polysaccharides to be prepared, characterized by opposite charges on the chain, in order that ionic interactions take place between them to form soluble complexes. In contrast to patent WO 2005/061611 which describes polyanion/neutral polysaccharide solutions, in the current case the present invention relates to solutions containing both polyanions and polycations which interact to form complexes that remain stable in solution.

Figure 6:
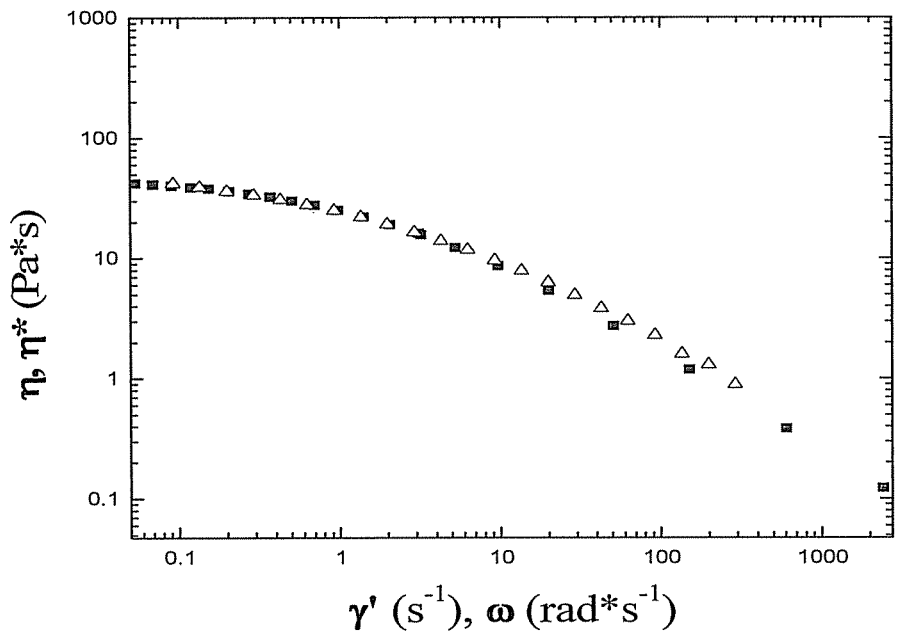
FIG. 6: Application of the Cox-Merz rule to the binary solution of hyaluronic acid (about 8-9×10⁵ $M_w$) and chitlac (ex. 19). Legend: (■) viscosity (η) as a function of deformation velocity (γ'), and (Δ) complex viscosity (η*) as a function of angular velocity (ω). Total polymer concentration 2%. Weight ratio of hyaluronic acid to chitlac=3:1 (hyaluronic acid 1.5% and chitlac 0.5%). Measurements were carried out by means of a StressTech rheometer (Reologica Instruments AB, 22363, Lund, Sweden) with a cone-plate geometry (50 mm radiusr, 1° angle) at 25° C.
Figure 7:
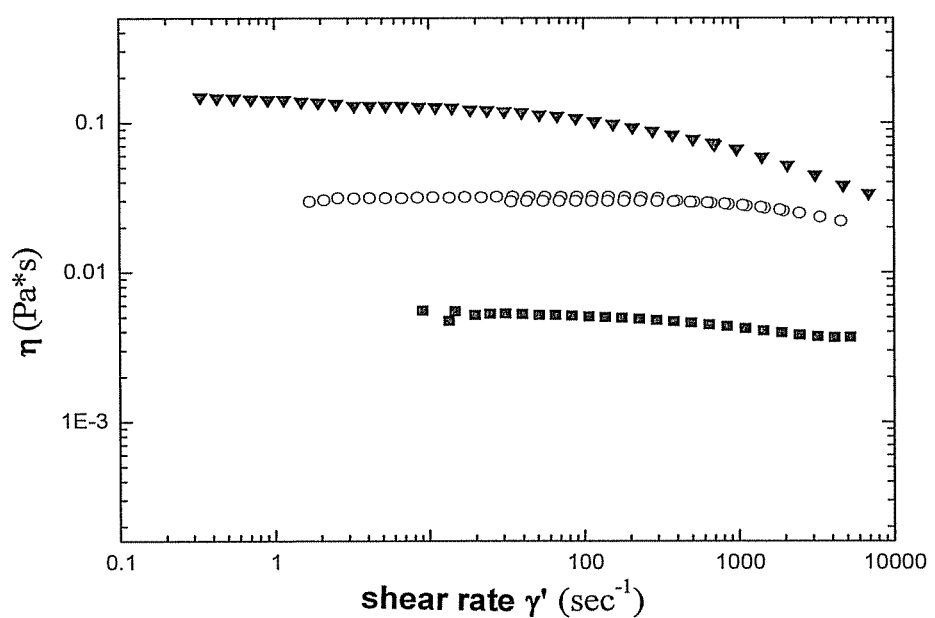
FIG. 7: (▼) Viscosity of a solution containing hyaluronic acid (~160,000 $M_w$) and chitlac (ex. 4). Total polymer concentration: 2%. Weight ratio of hyaluronic acid to chitlac=3:1 (hyaluronic acid 1.5% and chitlac 0.5%). (○) Viscosity of a hyaluronic acid solution (~160,000 $M_w$) at a 1.5% concentration. (■) Viscosity of a chitlac solution at a 0.5% concentration. Conditions: NaCl 0.15 M, Hepes 10 mM pH 7.4, 25° C. Measurements were carried out as previously described in FIG. 6.
Figure 8:
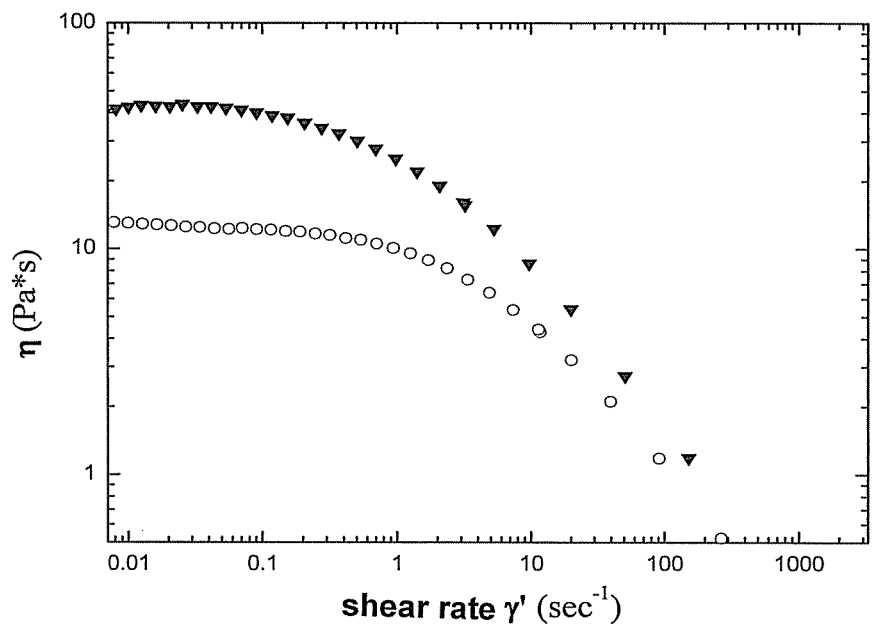
FIG. 8: (▼) Viscosity of a solution containing hyaluronic acid (~8-9×10⁵ $M_w$) and chitlac (ex. 19). Total polymer concentration: 2%. Weight ratio of hyaluronic acid to chitlac=3:1 (hyaluronic acid 1.5% and chitlac 0.5%). (○) Viscosity of a hyaluronic acid solution (~8-9×10⁵ $M_w$) at a 1.5% concentration. Conditions: NaCl 0.15 M, Hepes 10 mM, pH 7.4, 25° C. Measurements were carried out as previously described in FIG. 6.
Figure 9:
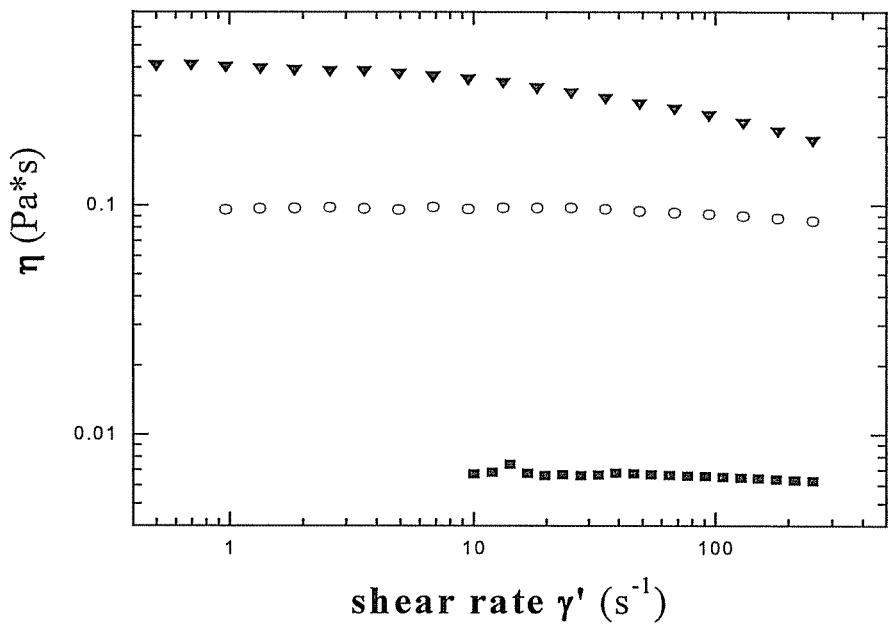
FIG. 9: (▼) Viscosity of a solution containing alginate (~130,000 $M_w$) and chitlac (ex. 20). Total polymer concentration: 2%. Weight ratio of alginate to chitlac=3:1 (alginate 1.5% and chitlac 0.5%). (○) Viscosity of an alginate solution (~130,000 $M_w$) at a 1.5% concentration. (■) Viscosity of a chitlac solution at a 0.5% concentration. Conditions: NaCl 0.15 M, Hepes 10 mM, pH 7.4, 25° C. Measurements were carried out as previously described in FIG. 6.
Figure 10:
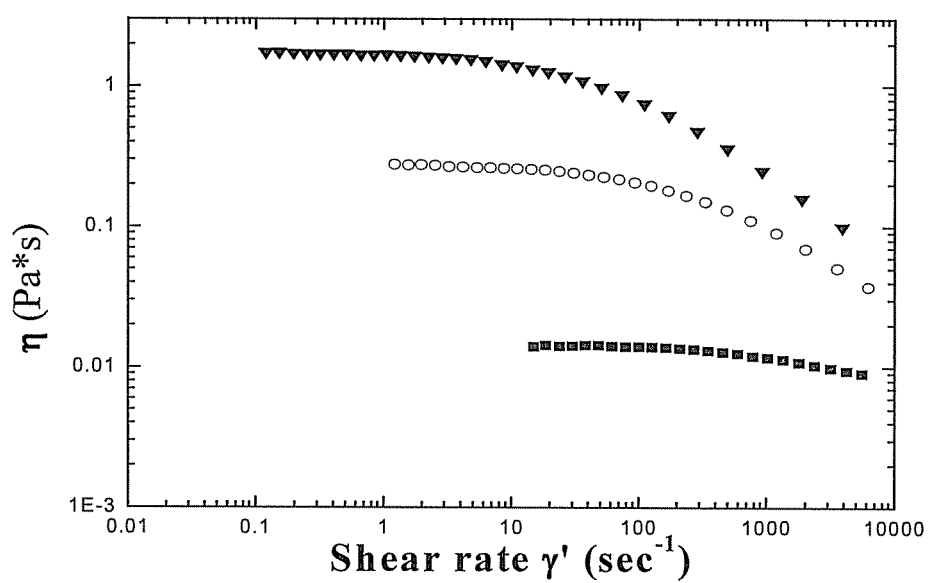
FIG. 10: (▼) Viscosity of a solution containing hyaluronic acid (~250,000 $M_w$) and chitlac (ex. 21). Total polymer concentration: 3%. Weight ratio of hyaluronic acid to chitlac=1:1 (hyaluronic acid 1.5% and chitlac 1.5%). (○) Viscosity of a hyaluronic acid (~250,000 $M_w$) solution at a 1.5% concentration. (■) Viscosity of a chitlac solution at a 1.5% concentration. Conditions: NaCl 0.15 M, Hepes 10 mM, pH 7.4, 25° C. Measurements were carried out as previously described in FIG. 6.

In this respect, FIG. 6 shows that the so called Cox-Merz rule, which predicts equality between the complex and absolute viscosities in a solution without "large scale" organization, can be applied to the binary solution containing hyaluronic acid and chitlac of example 19. Conversely, the presence of gels or microgels results in a deviation from this rule which is shown by the lack of equality between the two viscosities, complex and absolute, as measured with the rheometer.

Formation of soluble complexes between polyanions and oligosaccharide-modified chitosans can occur with either carboxylated or sulfated polysaccharides with average molecular weight varying up to 1,500 kDa.

The existence of interactions between positive charges on the oligosaccharide-modified chitosans and negative ones on the anionic polysaccharides (e.g. hyaluronic acid or alginate) also gives rise to an unexpected increase in the viscosity of the polymer solutions of anionic and cationic polysaccharide mixtures compared with the polymer solutions of the polysaccharides taken separately. In particular the viscosity of the aqueous solutions of the polymer mixture of polyanions and oligosaccharide-modified chitosans is found to be greater than the sum of the viscosities of the aqueous solutions of the individual constituent polymers of the mixture. FIGS. 7, 8, 9 and 10 clearly show this synergistic effect obtained with different polymers, with the polyanions and modified chitosan being at different w/w ratios.

Figure 11:
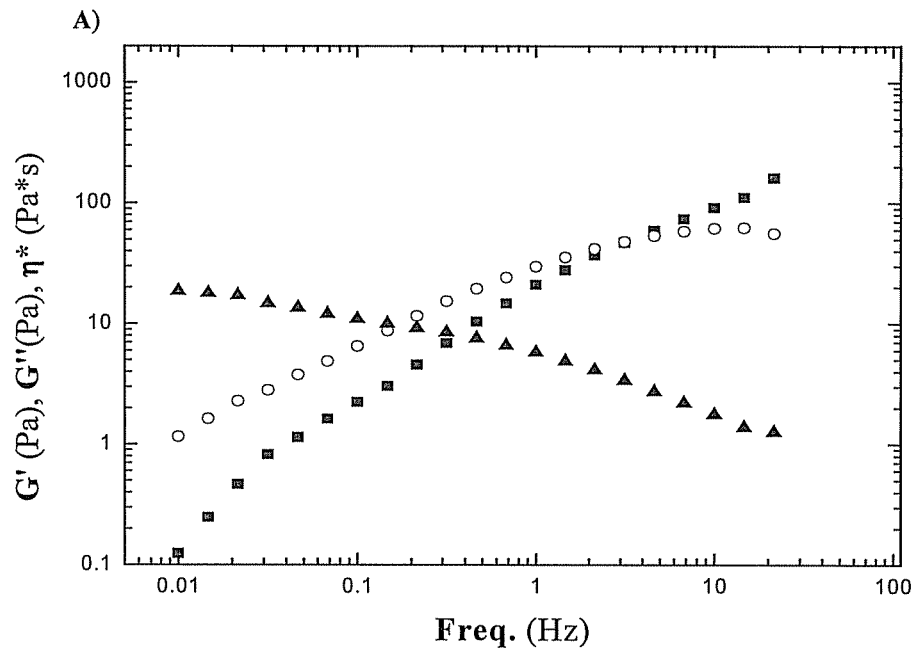
FIG. 11: Viscoelastic spectrum of A) a hyaluronic acid (~8-9×10⁵ $M_w$) solution (1.5%) and of B) a binary solution of hyaluronic acid and chitlac (ex. 19). Total polymer concentration 2%. Weight ratio of hyaluronic acid to chitlac=3:1 (hyaluronic acid 1.5% and chitlac 0.5%). Conditions: NaCl 0.15 M, Hepes 10 mM, pH 7.4, 25° C. Legend: (■)=G', (○)=G", (▲)=η*. Measurements were carried out by means of a StressTech rheometer (Reologica Instruments AB, 22363, Lund, Sweden) with a flat-cone geometry (50 nm beam, 10 aperture) within the frequency range 0.01-30 Hz at 25° C.
Figure 11:
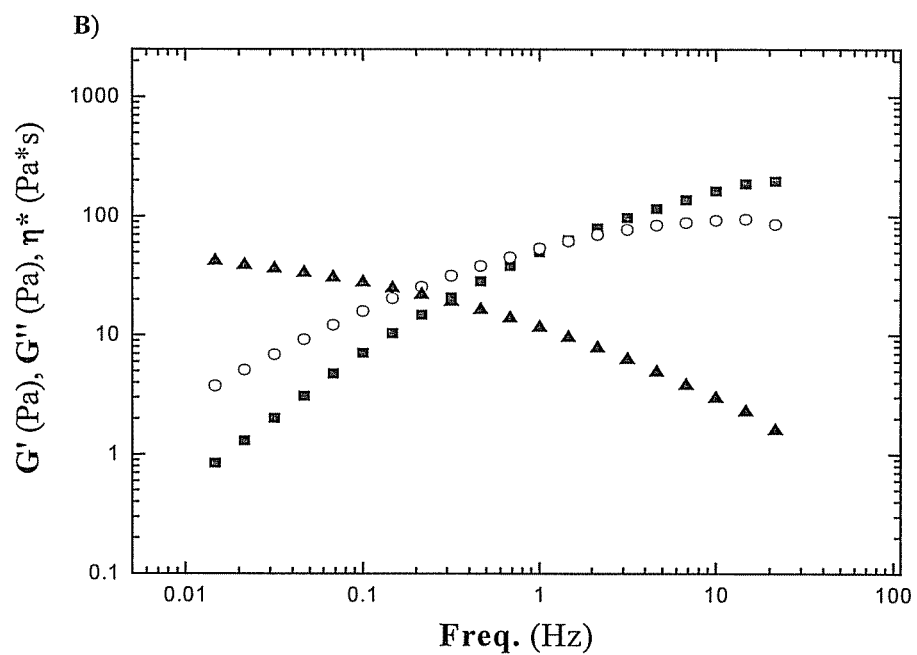

In addition said compositions also present a undoubted improvement in viscoelastic properties as inferred from FIG. 11. Indeed, the viscoelastic spectrum of the hyaluronic acid and chitlac binary solutions of example 19 given in FIG. 11B shows that the second polysaccharide not only does not significantly interfere with the viscoelastic properties of the hyaluronic acid but, rather, compared with the solution of hyaluronic acid alone (FIG. 11A), it reduces the frequency value at which G' and G" cross each other, i.e. the frequency at which the system starts to show properties which are more elastic than viscous. This effect is highly desirable for known applications of the polysaccharides and in particular in viscosupplementation for treatment of inflammatory and/or trauma-based osteo-articular pathologies, such as osteoarthritis, osteoarthrosis, meniscus and ligament ruption. For the purposes of the present invention the compositions of the invention can be used as such or in combination with suitable excipients or diluent for the preparation of products acceptable for administration to human and non-human mammals. For treating the above mentioned osteo-articular pathologies said products can be administered by the known intra-articular route. In addition and for the same reasons, the aforementioned compositions can be used in ophthalmic surgery.

The invention claimed is:

1. A polysaccharide composition comprising aqueous solutions of mixtures of at least one anionic polysaccharide and at least one oligosaccharide derivative of chitosan, wherein the at least one anionic polysaccharide has a molecular weight of at least 100 kDa;
   the chitosan derivatives have a degree of derivatization of at least 40% and
   the aqueous solutions have an ionic strength of at least 50 mM and not greater than 175 mM and a pH of at least 7 and
   wherein the at least one anionic polysaccharide and the at least one oligosaccharide derivative of chitosan remain in solution without phase separation and without formation of coacervates and the polysaccharide composition exhibits a synergistic increase of viscosity and viscoelasticity in comparison to the anionic polysaccharide.

2. The polysaccharide composition according to claim 1, wherein said ionic strength is 150 mM.

3. The polysaccharide composition according to claim 1, wherein said ionic strength is obtainable by means of addition of NaCl to obtain concentrations thereof in said aqueous solutions in a range comprised from 0.05 M and 0.175 M.

4. The polysaccharide composition according to claim 2, wherein said ionic strength is obtainable by means of addition of NaCl to obtain concentrations thereof in said aqueous solutions of 0.15 M.

5. The polysaccharide composition according to claim 1, wherein in the mixtures of at least one anionic polysaccharide and at least one oligosaccharide derivative of chitosan said anionic polysaccharides and said oligosaccharide derivatives of chitosan are in weight ratio range comprised from 10:1 to 1:1 of anionic polysaccharides to oligosaccharide derivatives of chitosan.

6. The polysaccharide composition according to claim 5, wherein in the mixtures of at least one anionic polysaccharide and at least one oligosaccharide derivative of chitosan said anionic polysaccharides and said oligosaccharide derivatives of chitosan are in a weight ratio range comprised from 3:1 to 1:1 of anionic polysaccharides to oligosaccharide derivatives of chitosan.

7. The polysaccharide composition according to claim 1, wherein the aqueous solutions of mixtures of at least one anionic polysaccharide and at least one oligosaccharide derivative of chitosan have a total polymer concentration within the range comprised from 1.5% (w/v) to 3% (w/v).

8. The polysaccharide composition according to claim 1, wherein the aqueous solutions of mixtures of at least one anionic polysaccharide and at least one oligosaccharide derivative of chitosan have a pH within the range comprised from 7 to 8.

9. The polysaccharide composition according to claim 1, wherein the aqueous solutions of mixtures of at least one anionic polysaccharide and at least one oligosaccharide derivative of chitosan have an osmolarity within the range comprised from 250 to 350 mM obtained by a further addition of non-ionic solutes.

10. The polysaccharide composition according to claim 9, wherein the non-ionic solute is mannitol.

11. The polysaccharide composition according to claim 1, wherein the degree of substitution of chitosan is within the range comprised from 50% to 80%.

12. The polysaccharide composition according to claim 11, wherein the degree of substitution of chitosan is 70%.

13. The polysaccharide compositions according to claim 1, wherein the oligosaccharide derivatives of chitosan are obtainable by derivatizing chitosan with oligosaccharides having from 2 to 4 glycosidic units.

14. The polysaccharide composition according to claim 13, wherein the oligosaccharides are selected from the group consisting of lactose, cellobiose, cellotriose, maltose, maltotriose, maltotetraose, chitobiose, chitotriose, melibiose.

15. The polysaccharide composition according to claim 13, wherein the oligosaccharide is lactose.

16. The polysaccharide composition according to claim 13, wherein the chitosan has an average molecular weight up to 1,500 kDa.

17. The polysaccharide composition according to claim 16, wherein the chitosan has an average molecular weight from 400 kDa to 1,000 kDa.

18. The polysaccharide composition according to claim 1, wherein the anionic polysaccharides are carboxylated or sulfated polysaccharides.

19. The polysaccharide composition according to claim 18, wherein the carboxylated polysaccharides are selected from the group consisting of hyaluronic acid, alginates, pectins, carboxymethylcellulose, xanthan.

20. The polysaccharide composition according to claim 18, wherein the carboxylated polysaccharide is hyaluronic acid.

21. The polysaccharide composition according to claim 18, wherein the sulfated polysaccharides are selected from the group consisting of carrageenans, agarose sulfate, keratan sulfate, dermatan sulfate, sulfated starch, heparin, heparan sulfate.

22. The polysaccharide composition according to claim 18, wherein the anionic polysaccharides have an average molecular weight up to 1,500 kDa.

23. The polysaccharide composition according to claim 22, wherein the anionic polysaccharides have an average molecular weight in a range comprised from 100 kDa to 1,000 kDa.

24. The polysaccharide composition according to claim 22, wherein the anionic polysaccharides have an average molecular weight of 900 kDa.

25. A method for biomedical applications in human or non-human mammals in need thereof comprising the administration of a polysaccharide compositions according to claim 1.

26. The method according to claim 25, wherein the application is viscosupplementation for treating inflammatory and/or traumatic osteoarticular pathologies.

27. The method according to claim 26, wherein said osteoarticular pathologies are selected from the group consisting of osteoarthritis, arthrosis or meniscus or ligament ruption.

28. The method according to claim 26, wherein the administration is by the intra-articular route.

29. The method according to claim 25, wherein the application is for ophthalmic surgery.

* * * * *